United States Patent
Schäfer et al.

(10) Patent No.: US 10,017,464 B2
(45) Date of Patent: Jul. 10, 2018

(54) PROCESS FOR PREPARING CYCLIC ALPHA-KETO ALCOHOLS FROM CYCLIC ALPHA-KETO ENOLS

(71) Applicant: BASF SE, Ludwigshafen (DE)

(72) Inventors: Bernd Schäfer, Dierbach (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/502,816

(22) PCT Filed: Jul. 31, 2015

(86) PCT No.: PCT/EP2015/067674
§ 371 (c)(1),
(2) Date: Feb. 9, 2017

(87) PCT Pub. No.: WO2016/023772
PCT Pub. Date: Feb. 18, 2016

(65) Prior Publication Data
US 2017/0217884 A1    Aug. 3, 2017

(30) Foreign Application Priority Data
Aug. 12, 2014 (EP) .................................. 14180725

(51) Int. Cl.
*C07C 403/24* (2006.01)
*C07C 403/08* (2006.01)

(52) U.S. Cl.
CPC .......... *C07C 403/24* (2013.01); *C07C 403/08* (2013.01); *C07B 2200/07* (2013.01); *C07C 2601/16* (2017.05)

(58) Field of Classification Search
CPC .. C07C 403/24; C07C 403/08; C07C 2601/16
USPC ...................................................... 568/347
See application file for complete search history.

(56) References Cited

U.S. PATENT DOCUMENTS

| 4,283,559 | A | 8/1981 | Broger et al. |
| 5,625,099 | A | 4/1997 | Ernst et al. |
| 6,590,111 | B2 | 7/2003 | Grimmer et al. |
| 6,699,911 | B2 | 3/2004 | Grimmer et al. |
| 2006/0088905 | A1 | 4/2006 | Lockwood et al. |

FOREIGN PATENT DOCUMENTS

| DE | 10049271 A1 | 4/2002 |
| EP | 0005748 A2 | 12/1979 |
| EP | 0633258 A1 | 1/1995 |
| EP | 1285912 A2 | 2/2003 |

OTHER PUBLICATIONS

Widmer et al. Technical Procedures for the Synthesis of Carotenoids and Related Compounds from 6-oxo-isophorone. V. Synthesis of Astacene. Helvetica Chemica Acta, vol. 65, No. 67, 1982.*
Francis, G., et al., "Animal Carotenoids: 6. The Structures of Roserythrin and the Parent Nor-Carotenoid", Acta Chemica Scandinavica, vol. 26, No. 3, (1972), pp. 1097-1104.
Hall, E., et al., "Electrochemical Reductive Acylation of Astacene; a Route to the Cartenoid Astaxanthin", Journal of the Chemical Society, Chemical Communications, No. 9, (1978), pp. 387-388.
International Search Report for PCT/EP2015/066902 dated Oct. 1, 2015.
International Search Report for PCT/EP2015/067674 dated Oct. 15, 2015.
Widmer, E., et al., "Technische Verfahren zur Synthese von Carotinoiden und verwandten Verbindungen aus 6-Oxo-isophoron. V. Syntese von Astacin", Helvetica Chimica Acta, vol. 65, No. 3, (1982), pp. 671-683.
Written Opinion of the International Searching Authority for PCT/EP2015/066902 dated Oct. 1, 2015.
Written Opinion of the International Searching Authority for PCT/EP2015/067674 dated Oct. 15, 2015.
Zell, R., et al., "Technische Verfahren zur Synthese von Carotinoiden und verwandten Verbindungen aus 6-Oxo-isophoron. III. Ein neues Konzept für die Synthese der enantiomeren Astaxanthine", Helvetica Chimica Acta, vol. 64, No. 7, (1981), pp. 2447-2462.
Widmer, E, et al., "Technical procedures for the synthesis of carotenoids and related substances compounds of 6-0x0-isophorone. V. Synthesis of AstacinI", Helvetica Chimica Acta, vol. 65, No. 3, (1982), pp. 671-683, machine translation.

* cited by examiner

Primary Examiner — Sikarl A Witherspoon
(74) Attorney, Agent, or Firm — Drinker Biddle & Reath LLP

(57) ABSTRACT

The invention relates to a method for preparing a cyclic α-ketoalcohol, particularly a 6-hydroxycyclohexenone from a cyclic α-ketoenol, particularly a 6-hydroxycyclohexadienone, using a reducing agent. This reducing agent is selected from hydrogen gas; a secondary alcohol, formic acid and the salts of formic acid or a mixture of at least two representatives of these compound classes. The invention further comprises the use of an α-ketoenol, in particular a 6-hydroxycyclohexadienone, as intermediate for preparing astaxanthin.

22 Claims, No Drawings

PROCESS FOR PREPARING CYCLIC ALPHA-KETO ALCOHOLS FROM CYCLIC ALPHA-KETO ENOLS

CROSS-REFERENCE TO RELATED APPLICATIONS

This application is a national stage application (under 35 U.S.C. § 371) of PCT/EP2015/067674, filed Jul. 31, 2015, which claims benefit of European Application No. 14180725.5, filed Aug. 12, 2014, both of which are incorporated herein by reference in their entirety.

The present invention relates to a method for preparing cyclic α-ketoalcohols from cyclic α-ketoenols or their tautomeric α-diketones, particularly comprising a 6-hydroxycyclohexadienone as starting compound. The present invention further comprises the use of cyclic α-ketoenols for preparing astaxanthin in various isomeric forms.

Industrial syntheses of astaxanthin have been described in detail both in the relevant literature, e.g. G. Britton, S. Liaaen-Jensen, H. Pfander, Carotenoids, Vol. 2, Birkhäuser Verlag, Basel, 1996, 283 ff., in various textbooks, e.g. B. Schäfer, Naturstoffe der chemischen Industrie (Natural Substances of the Chemical Industry), Akademischer Verlag, Heidelberg, 2007, 427 ff., in scientific journals, e.g. K. Meyer, Chemie in unserer Zeit (Chemistry in Our Time) 36 (2002) 178 and also in the patent literature, e.g. DE 10049271 A1 or EP 1285912 A2. Practically all astaxanthin syntheses pass through C15 intermediates, which are saturated in position $\Delta^{5,6}$, bearing an alcohol function respectively in position 6.

However, in the synthesis of these C15 intermediates saturated in position $\Delta^{5,6}$, such C15 intermediates also arise that are unsaturated in position $\Delta^{5,6}$, such as the compound L1:

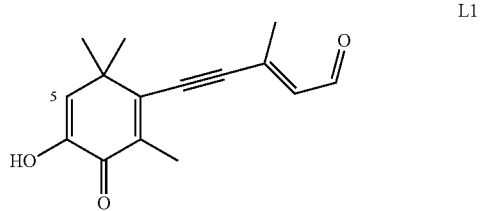 [SMILES: CC1=C(C#C/C(C)=C/C=O)C(C)(C)C=C(O)C1=O]

However, according to the remarks in E. Widmer, R. Zell, T. Lukáč, M. Casadei, P. Schönholzer and E. A. Broger, Helv. Chim. Acta 64 (1981) 2405, compound L1 is undesirable since it significantly reduces the yield of the desired astaxanthin precursor (compound 20) (see p. 2407, scheme 4 and p. 2408, section 2).

B. G. Britton, S. Liaaen-Jensen, H. Pfander, Carotenoids, Vol. 2, Birkhäuser Verlag, Basel, 1996 also draws attention to this disadvantage, since in the last paragraph on p 284 it states: "In syntheses of astaxanthin (406), it must be remembered that all products with the partial structure 83 can irreversibly form diosphenol structures 84 under the action of strong acids or bases. In addition, oxidation to give the enolized 1,2-diketone 85 readily occurs [90] Scheme 26

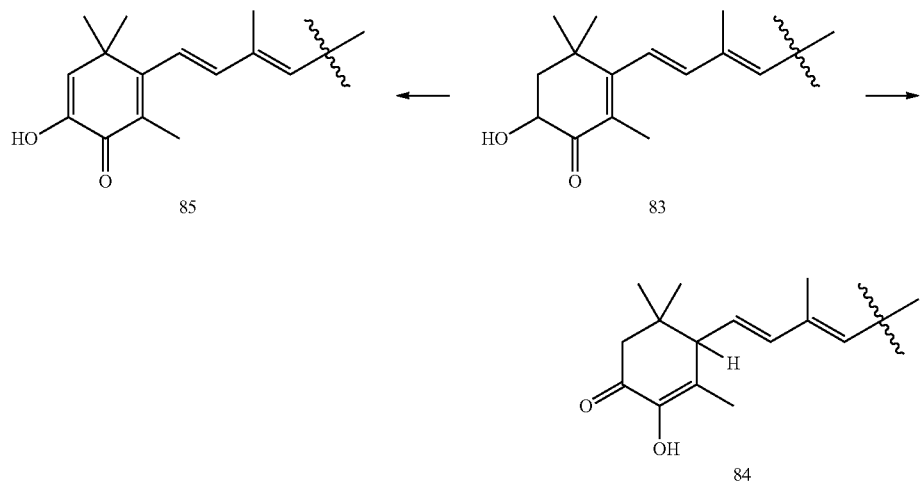

Although C15 intermediates such as L1 and 85, unsaturated in position $\Delta^{5,6}$, are repeatedly described as disadvantageous in the literature, no route has yet been found to convert them back again into C15 intermediates having a 6-hydroxycyclohex-2-en-1-one base structure. In addition, the selective hydrogenation of the double bond in position 5 of a 2,4,4-trimethylcyclohexa-2,5-dien-1-one system, particularly the compounds of the formulae 2a and 2b, is to date totally unknown. The following statement is found only in E. Widmer, T. Lukáč, K. Bernhard, R. Zell, Helv. Chim. Acta 65 (1982) 671:

"Astacin is of particular interest as potential starting material for the synthesis of astaxanthin. However, no method for the regioselective hydrogenation of the 2,3-double bond is known to date. An electrochemical reduction under acylating conditions has already been achieved, however, which allowed the isolation of astaxanthin in a yield of 10%" [E. A. H. Hall, G. P. Moss, J. H. P. Utley, B. C. L. Weedon, Chem. Commun. (1978) 387]. Astacin has the structural formula L2 comprising 40 carbon atoms referred to below and cannot be compared to a C15 intermediate, i.e. a building block of only 15 carbon atoms.

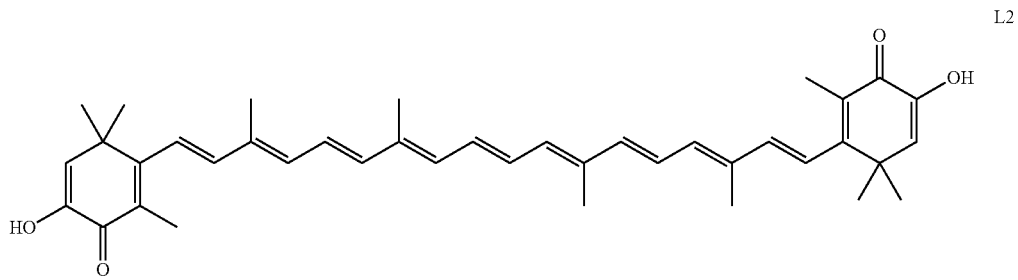 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

Moreover, the yields of astacin L2 obtained of 10% in a mixture are unsuitable for industrial or routine production.

Against this background, an object to be achieved for those skilled in the art consists in finding a route to selectively convert cyclic α-ketoenols or tautomeric α-diketones thereof to cyclic α-ketoalcohols. Selectively means that functional groups present, other than the enol group in the α-ketoenol—or the corresponding keto group in the α-diketone—do not react or only react to a very low extent. A method should also be found which can convert 6-hydroxy-cyclohexadienones, particularly those having 15 carbon atoms, into the corresponding 6-hydroxycyclohexenones, without noticeable reaction of other functional groups in the 6-hydroxycyclohexadienone, preferably none at all. In particular, a method should be established that allows 6-hydroxy-3-[(1E/Z)-3-hydroxy-3-methylpenta-1,4-dienyl]-2,4,4-trimethylcyclohexa-2,5-dien-1-one or 6-hydroxy-3-[(1E/Z,3E/Z)-5-hydroxy-3-methylpenta-1,3-dienyl]-2,4,4-trimethylcyclohexa-2,5-dien-1-one to be selectively converted into the corresponding 6-hydroxycyclohexenone. This method should be feasible with simple apparatus and on an industrial scale. It should also be inexpensive and simple to perform, i.e. to proceed without many intermediates or complex method steps and workup steps.

A further object consists of the stereoselective conversion of cyclic α-ketoenols (or α-diketones) such as 6-hydroxy-cyclohexadienones, in particular 6-hydroxy-3-[(1E/Z)-3-hydroxy-3-methylpenta-1,4-dienyl]-2,4,4-trimethylcyclohexa-2,5-dien-1-one or 6-hydroxy-3-[(1E/Z,3E/Z)-5-hydroxy-3-methylpenta-1,3-dienyl]-2,4,4-trimethylcyclohexa-2,5-dien-1-one, that is to say, a conversion such that to a large degree, and as far as possible, only one stereoisomer is formed as target compound in each case. The stereoselective reactions should also be simple to perform and applicable on an industrial scale. The conversions should also comprise as few method steps and workup steps as possible and be cost-effective.

A final object consists of providing a novel precursor as starting material for the synthesis of astaxanthin, in which the asymmetric center in position 3 of the astaxanthin is optionally racemic or has (S) or (R) configuration.

The main features of the achievement of these objects of the invention are obtained from claims 1 and 15. Configurations are the subject matter of claims 2 to 14.

The objects mentioned above are achieved by a method for preparing a 6-hydroxycyclohexenone selected from the group consisting of 6-hydroxy-3-[(1E/Z)-3-hydroxy-3-methylpenta-1,4-dienyl]-2,4,4-trimethylcyclohex-2-en-1-one of the formula 1a and 6-hydroxy-3-[(1E/Z,3E/Z)-5-hydroxy-3-methylpenta-1,3-dienyl]-2,4,4-trimethylcyclohex-2-en-1-one of the formula 1b

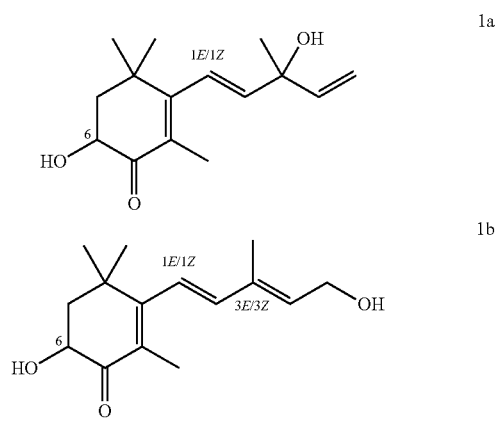

in which the asymmetric center in position 6 is racemic or has (S) or (R) configuration. This method according to the invention is characterized in that a 6-hydroxycyclohexadienone selected from the group consisting of 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula (2b)

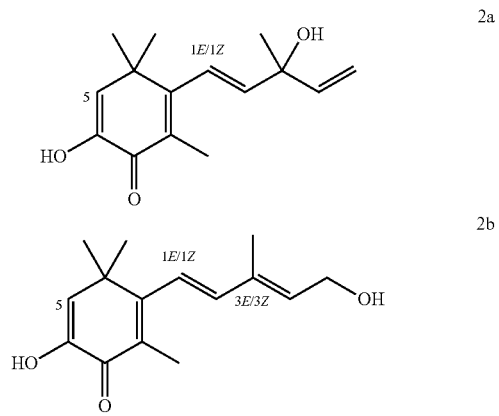

is reacted non-stereoselectively or stereoselectively with a reducing agent.

Such a result could not have been predicted since, in addition to the enolized carbonyl in position 6, a person skilled in the art would assume that at least one of the other functional groups of the compounds 2a or 2b, i.e. the carbonyl in position 1 and/or at least one of the exocyclic double bonds and/or the exocyclic hydroxyl group, would likewise be reduced. A person skilled in the art would expect that the triol below is formed with nickel catalysts and the compound A is formed with Pd.

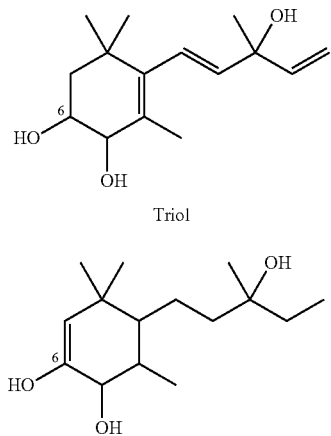

Triol

A

"Non-stereoselectively" means that the reaction of the reactant due to the reducing agent leads to a product with no steric preference.

"Stereoselectively" is understood to mean that the reducing agent gives rise to products, namely enantiomers or diastereomers, in which predominantly only one configuration, as far as possible exclusively one configuration, is formed at the site of reduction (at the stereocenter).

The cyclic α-ketoenols used as starting compounds according to the invention, particularly the 6-hydroxycyclohexadienones 2a and 2b, may also be regarded as tautomeric diketones according to the equilibrium shown below.

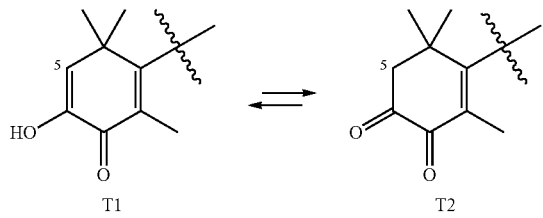

T1                    T2

In the context of this invention, therefore, the term "cyclic α-ketoenol" includes not only the tautomer T1 but in each case always the tautomer T2 as well. It is not mandatory, however, that the tautomers T1 and T2 comprise cyclic methyl groups as shown above.

The term reducing agent comprises all those compounds which are suitable for converting a cyclic α-ketoenol into the corresponding alcohol. In a preferred continuation, the term reducing agent is understood to mean all those compounds which convert a cyclic α-ketoenol into the corresponding alcohol, without the other functional groups of the reactant, in particular a 6-hydroxycyclohexadienone and especially the compounds 2a, 2b, also being converted.

A continuation of the invention provides that the reducing agent is at least one compound selected from the group consisting of hydrogen gas; a secondary alcohol, preferably isopropanol or butan-2-ol; formic acid, the salts of formic acid, particularly an alkali metal, alkaline earth metal or ammonium formate or a mono-, di-, tri- or tetra(C1-C4)-alkylammonium formate.

A secondary alcohol is a compound in which two alkyl groups are located on the carbon atom in the ipso position, wherein alkyl includes any group with the overall formula $C_nH_{2n+1}$. Secondary alcohols are selected from the group consisting of propan-2-ol, butan-2-ol, 3-methylbutan-2-ol, 3,3-dimethylbutan-2-ol, pentan-2-ol, pentan-3-ol, 2-methylpentan-3-ol, 3-methylpentan-2-ol, 4-methylpentan-2-ol, 2,2-dimethylpentan-3-ol, 2,4-dimethylpentan-3-ol, 3,3-dimethylpentan-2-ol, 4,4-dimethylpentan-2-ol, 2,2,4-trimethylpentan-3-ol, 2,2,4,4-tetramethylpentan-3-ol, hexan-2-ol, hexan-3-ol, 2-methylhexan-3-ol, 3-methylhexan-2-ol, 4-methylhexan-2-ol, 4-methylhexan-3-ol, 4-ethylhexan-3-ol, 5-methylhexan-2-ol, 5-methylhexan-3-ol, 2,2-dimethylhexan-3-ol, 2,4-dimethylhexan-3-ol, 2,5-dimethylhexan-3-ol, 4-isopropyl-2-methylhexan-3-ol, 2,2,5,5-tetramethylhexan-3-ol, heptan-2-ol, heptan-3-ol, 2-methylheptan-3-ol, 2-methylheptan-4-ol, 3-methylheptan-2-ol, 4-methylheptan-2-ol, 4-methylheptan-3-ol, 4-ethylheptan-3-ol, 5-methylheptan-2-ol, 5-methylheptan-3-ol, 6-methylheptan-2-ol, 2,2-dimethylheptan-3-ol, 2,6-dimethylheptan-2-ol, 2,6-dimethylheptan-4-ol, 3,5-dimethylheptan-4-ol, 3,6-dimethylheptan-2-ol, 2,5,6-trimethylheptan-4-ol, octan-2-ol, octan-3-ol, octan-4-ol, 2-methyloctan-4-ol, 2-methyloctan-5-ol, 3-methyloctan-2-ol, 3-methyloctan-4-ol, 2,2-dimethyloctan-3-ol, 2,4-dimethyloctan-3-ol, 2,6-dimethyloctan-3-ol, 3,7-dimethyloctan-2-ol, nonan-2-ol, nonan-4-ol, nonan-5-ol, nonan-3-ol, 2-methylnonan-4-ol, 2-methylnonan-3-ol, 3-methylnonan-2-ol, 5-methylnonan-4-ol, 5-ethylnonan-2-ol, 5-butylnonan-2-ol, 2,2-dimethylnonan-3-ol, 2,6,8-trimethylnonan-4-ol, decan-2-ol, decan-3-ol, decan-4-ol, decan-5-ol, 2-methyldecan-3-ol, 5-methyldecan-4-ol, undecan-2-ol, undecan-3-ol, undecan-5-ol, undecan-6-ol, 2-methylundecan-3-ol, 5-methylundecan-6-ol, 6-methylundecan-5-ol, 6-pentylundecan-5-ol, 7-ethyl-2-methylundecan-4-ol, dodecan-2-ol, dodecan-3-ol, dodecan-5-ol, dodecan-6-ol, 2-methyldodecan-3-ol, 3,7,11-trimethyldodecan-4-ol, tridecan-2-ol, tridecan-3-ol, tridecan-4-ol, tridecan-7-ol, 2-methyltridecan-3-ol, tetradecan-2-ol, tetradecan-3-ol, tetradecan-4-ol, tetradecan-6-ol, 2-methyltetradecan-3-ol, 3,7-dimethylpentadecan-2-ol, 6,10,14-trimethylpentadecan-2-ol, hexadecan-2-ol, hexadecan-6-ol, 9-octylheptadecan-10-ol, dicapryl alcohol.

Among these secondary alcohols, preference is given to the alcohols isopropanol and/or butan-2-ol, since they are inexpensive and on reduction form acetone or methyl ethyl ketone, two solvents which can be readily removed due to their low boiling points. Moreover, as polar aprotic solvents they dissolve many 6-hydroxycyclohexadienones, for example, the compounds 2a and 2b.

In a further configuration, the reducing agent is preferably at least one compound selected from the group of formic acid and/or salts of formic acid. These compounds are inexpensive to acquire. Moreover, carbon dioxide is released on reduction thereof, which can be released continuously from the reaction vessel without much difficulty or released at the end of the reaction. In relation to the apparatus, a simple and targeted reaction procedure is possible. In addition, the workup of the reaction mixture is considerably simplified and thus the costs of the preparation process are reduced.

Salts of formic acid are all those compounds comprising a formate anion and an organic or inorganic cation as counterion.

A mono-, di- or tri- or tetra(C1-C4)-alkylammonium formate comprises a formate anion and a nitrogen-bearing cation as counterion. The nitrogen-bearing cation is an ammonium ion, which comprises four hydrogen atoms in addition to the nitrogen or has one (mono), two (di), three (tri) or four (tetra) alkyl groups instead of hydrogen. The at least one alkyl group is a C1-C4-alkyl group, i.e. it is selected from methyl, ethyl, n-propyl, isopropyl, n-butyl, sec-butyl, isobutyl, tert-butyl.

Particularly suitable and inexpensive formic acid salts for the method according to the invention include trimethylammonium formate, triethylammonium formate, tri-n-butylammonium formate, ethyldiisopropylammonium formate, tetrabutylammonium formate or a mixture of at least two of these salts.

The reducing agent is particularly preferably an alkali metal salt or an alkaline earth metal salt or an ammonium salt of formic acid or a mixture of at least two of these compounds. In addition to the gaseous carbon dioxide, by-products occur in the reduction with one of these reducing agents which are either present dissolved in a polar phase or are precipitated in the form of a salt. Removal from the reaction product is thereby particularly simple.

In a particularly developed preferred embodiment, the reducing agent is at least one compound selected from the group consisting of sodium formate, potassium formate, magnesium formate, calcium formate and from the ammonium salts, from ammonia, i.e. ammonium formate. These reducing agents have in common that they are very inexpensive, since the formates of sodium, potassium, magnesium and calcium, and also those of ammonia are readily accessible and are available from various suppliers. Ammonium formate also has the advantage that ammonia is liberated at elevated temperature. From this perspective, excess ammonium formate can be decomposed and removed at the end of the reduction by heating.

In a further variant, the reducing agent is selected from the group of the formates of primary amines, in particular from the formate of at least one of the amines methylamine, ethylamine, n-propylamine, isopropylamine, n-butylamine, sec-butylamine, tert-butylamine, isobutylamine, n-pentylamine, aniline, benzylamine.

In another configuration of the invention, the reducing agent is at least one compound selected from the group consisting of secondary or tertiary amines of formic acid. Secondary amines of formic acid are formed from a formate ion as anion and a simple protonated N,N-dialkylamine as cation.

Secondary amines of formic acid comprise the formate of dimethylamine, of diethylamine, of di-n-propylamine, of di-n-butylamine or a mixture of at least two of these compounds.

Tertiary amines of formic acid consist of a formate ion as anion and a simple protonated N,N,N-trialkylamine as cation.

Tertiary amines of formic acid comprise the formate of trimethylamine, of triethylamine, of tri-n-propylamine, of tri-n-butylamine, of ethyldiisopropylamine or a mixture of at least two of these compounds.

In another modification of the invention, the reducing agent is at least one compound selected from the group of quaternary ammonium salts of formic acid. Quaternary ammonium salts of formic acid are compounds consisting of a formate ion as anion and an N,N,N,N-tetraalkylammonium ion as cation.

Quaternary salts of formic acid comprise, for example, tetraethylammonium formate, tetrabutylammonium formate, triisopropylethylammonium formate.

In a further configuration, the reducing agent is preferably at least one compound selected from the group of the salts of formic acid, in which the salts are generated in situ by neutralization of formic acid with an appropriate base. This base is selected from the group of ammonia and/or primary amines and/or secondary amines and/or tertiary amines. Salts generated in this way from formic acid are always particularly of advantage if the salt is only to be formed slowly or if salt compounds which are not readily commercially available are to be used.

In a further configuration, the reducing agent is preferably at least one compound selected from the group of the salts of formic acid, in which the salts are used as such. Such salts have always proven to be favourable if they are obtainable inexpensively and can be easily stored and a reaction-dependent minimum or maximum concentration of these salts does not have to be regulated by in situ formation.

The method according to the invention is pursued in that the cyclic α-ketoenol, in particular the 6-hydroxycyclohexadienone, is reacted non-stereoselectively or stereoselectively with the reducing agent in the presence of a transition metal catalyst; preferably in the presence of an achiral or optically active transition metal catalyst. This means that the object formulated above was achieved in a further inventive version by a transition metal-catalyzed hydrogenation, wherein the catalysts used are optionally achiral, enantiomerically enriched or enantiomerically pure transition metal catalysts. These catalysts significantly accelerate the reduction according to the invention and thus contribute to cost reduction.

A transition metal catalyst is understood to mean a compound which accelerates a reaction. Said catalyst comprises at least one transition metal, i.e. at least one metal of the third to twelfth group of the periodic table and at least one ligand.

An optically active transition metal catalyst is likewise a compound which accelerates a reaction. Said catalyst comprises at least one transition metal of the third to twelfth group of the periodic table and at least one optically active ligand.

Optically active ligands are those ligands which are capable of rotating, to a greater or lesser extent, the plane of polarization of a beam of linearly polarized light.

It has been shown that the transition metal catalyst having a transition metal selected from the group consisting of Ti, Zr, Hf, V, Nb, Ta, Cr, Mo, W, Mn, Re, Fe, Ru, Os, Co, Rh, Ir, Ni, Pd, Pt, Cu, Ag and Au could be used for the method according to the invention. The transition metals Zr, Nb, Mo, W, Ru, Co, Rh, Ir, Ni, Pd are particularly suitable by reason of their relative availability and/or their reactivity, particularly the transition metals Mo, Ru, Co, Rh, Ir, Ni, Pd. Particularly good results were obtained with the transition metals Ru, Ir, Ni, Pd in appropriate ligand arrangements. Finally, in the experiments conducted, ruthenium (Ru) has proven to be particularly suitable for the method according to the invention, since high yields of 6-hydroxycyclohexenone, particularly of compound 1a, 1b are obtained, without noticeable reaction, as far as possible no reaction at all, of the carbonyl group at position 1 and other functional groups of the 6-hydroxycyclohexadienones, particularly of the starting compounds 2a, 2b.

The transition metal catalyst, which is suitable for the reduction of the double bond at position $\Delta^{5,6}$ (equivalent to a keto group in position 6) of the 6-hydroxycyclohexadieneones, particularly the compounds 2a, 2b, to give the corresponding secondary alcohol, preferably comprises a transition metal atom and at least one optionally achiral or optically active ligand. In principle, it is possible to use all transition metals which can form a suitable transition metal catalyst as transition metal atom, such as Ti, Zr, Hf, V, Nb, Ta, Cr, Mo, W, Mn, Re, Fe, Ru, Os, Co, Rh, Ir, Ni, Pd, Pt, Cu, Ag or Au.

A further provision of the inventive method is that the transition metal catalyst comprises at least one ligand selected from amines and/or phosphanes. In particular, the ligand is selected from amines and/or phosphanes and/or aromatic compounds and/or halides. In this case, the aromatic compounds are bonded to the transition metal in complex form and optionally covalently bonded to an amine or phosphane ligand. That is to say, such species have proven to be particularly suitable as far as coordination with a transition metal is concerned.

In particular, it has been found that the cyclic α-ketoenol, particularly the 6-hydroxycyclohexadienone, is then reacted particularly non-stereoselectively or stereoselectively with the reducing agent in the presence of a transition metal catalyst; preferably in the presence of an optically active transition metal catalyst, when the transition metal of the transition metal catalyst is ruthenium (Ru) and the ligand is selected from amines.

The phosphane ligand is preferably a phosphane of the general formula 3,

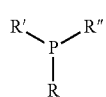

where R, R' and R" are each independently selected from the group consisting of one of the residues C1-C4-Alkyl, phenyl, mono- up to tri-C1-C4-Alkyl-substituted aryl; preferably a triarylphosphane and especially preferably triphenylphosphane.

C1-C4-Alkyl is a group selected from methyl, ethyl, n-propyl, isopropyl, n-butyl, sec-butyl, isobutyl, tert-butyl. Aryl comprises all aromatic base structures, particularly phenyl and benzyl. C1-C4-Alkyl-substituted aryl is an aryl, as previously defined, which is linked to one, two, three or four or five C1-C4-alkyl residues, as previously defined.

The following configuration of the method according to the invention affords protection of an outstanding aspect. Said configuration claims that the transition metal catalyst comprises at least one ligand selected from the group consisting of H$_2$N—CH$_2$—CH$_2$—OH, MeHN—CH$_2$—CH$_2$—OH, H$_2$N—CHH$_2$—NH$_2$, TsNH—CH$_2$—CH$_2$—NH$_2$, TsNH—CH$_2$—CH$_2$—NH—(CH$_2$)$_n$—O$_m$—(CH$_2$)$_o$-aryl where n=1-4, m=0 or 1 and o=1-4 and aryl=phenyl or mono-, di-, tri-C1-C4-alkylphenyl, optically active compound. To be specific, with this type of ligand, a yield of 6-hydroxycyclohexenones, in particular the compounds 1a, 1b, of 85% could be achieved from the corresponding 6-hydroxycyclohexadienones, in particular the compounds 2a, 2b, as is shown below in example 1.

A particular development of the invention thus provides a method for preparing a cyclic α-ketoalcohol, in particular a 6-hydroxycyclohexenone, selected from the group consisting of 6-hydroxy-3-[(1E/Z)-3-hydroxy-3-methylpenta-1,4-dienyl]-2,4,4-trimethylcyclohex-2-en-1-one of the formula 1a and 6-hydroxy-3-[(1E/Z,3E/Z)-5-hydroxy-3-methylpenta-1,3-dienyl]-2,4,4-trimethylcyclohex-2-en-1-one of the formula 1b

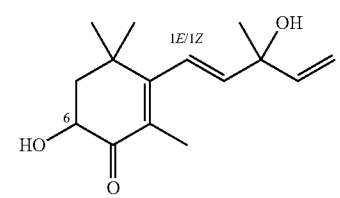

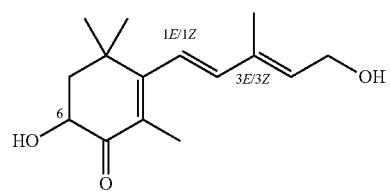

in which the asymmetric center in position 6 is racemic or has (S) or (R) configuration, wherein a cyclic α-ketoenol, in particular a 6-hydroxycyclohexadienone, selected from the group consisting of 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula 2b

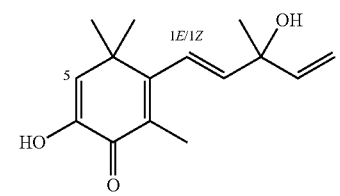

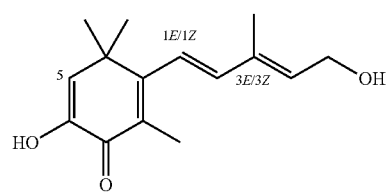

is reacted non-stereoselectively or stereoselectively with a reducing agent selected from the group consisting of formic acid and/or the salts of formic acid, isopropanol, butan-2-ol, in the presence of a transition metal catalyst, wherein the transition metal catalyst comprises ruthenium (Ru) as transition metal and at least one ligand selected from the group consisting of H$_2$N—CH$_2$—CH$_2$—OH, MeHN—CH$_2$—CH$_2$—OH, H$_2$N—CH$_2$—CH$_2$—NH$_2$, TsNH—CH$_2$—CH$_2$—NH$_2$, TsNH—CH$_2$—CH$_2$—NH—(CH$_2$)$_n$—O$_m$—(CH$_2$)$_o$-aryl where n=1-4, m=0 or 1 and o=1-4 and aryl=phenyl or mono-, di-, tri-C1-C4-alkylphenyl, optically active compound.

According to this method according to the invention, which describes a non-stereoselective reduction and in the case of the optically active compound either a non-stereoselective or a stereoselective reduction, racemic mixtures of cyclic α-ketoalcohols, particularly 6-hydroxycyclohexenones, are produced which are sufficient for many applications.

The transition metal catalysts required for the racemic mixtures can be generated, for example, by reacting a suitable ruthenium compound, such as, for example [RuX$_2$ ($\eta^6$-Ar)]$_2$, with a suitable ligand, where X is a halogen atom such as fluorine, chlorine, bromine or iodine, and Ar is benzene or a substituted benzene derivative, in particular a benzene derivative substituted with C1-C4-alkyl residues. C1-C4-Alkyl is as already defined above.

However, there is also a requirement for optically active α-ketoalcohols, particularly 6-hydroxycyclohexenones.

In the method according to the invention, therefore, an optically active transition metal catalyst is particularly preferably used which comprises a transition metal atom and at least one optically active ligand, wherein the transition metal atom is ruthenium (Ru). This means that the cyclic α-ketoenol, in particular the 6-hydroxycyclohexadienone, is reacted stereoselectively with the reducing agent in the presence of an optically active transition metal catalyst, wherein the transition metal catalyst comprises a transition metal atom and at least one optically active ligand and the transition metal atom is ruthenium (Ru).

Preferred chiral, particularly optically active ruthenium catalysts can be generated, for example, by reacting a suitable ruthenium compound, such as, for example [RuX$_2$($\eta^6$-Ar)]$_2$, with a suitable chiral, particularly optically active ligand, where X is a halogen atom such as fluorine, chlorine, bromine or iodine, and Ar is benzene or a substituted benzene derivative, in particular a benzene derivative substituted with C1-C4-alkyl residues. C1-C4-Alkyl is as already defined above.

The chiral, particularly optically active ruthenium catalyst is preferably characterized in that the optically active ligand is an optically active amine or an optically active amino acid. Examples of optically active amines, which may be reacted with a suitable ruthenium compound, in particular [RuX$_2$($\eta^6$-Ar)]$_2$, to give the catalytically active complex, are H$_2$N—CHPh-CHPh-OH, H$_2$N—CHMe-CHPh-OH, MeHN—CHMe-CHPh-OH, TsNH—CHPh-CHPh-NH$_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide or N-[(1R,2R)-1,2-diphenyl-2-(2-(4-methylbenzyloxy)ethylamino)ethyl]-4-methylbenzene sulfonamide, particularly (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylenzyloxy)ethylamino)ethyl]-4-methylbenzene sulfonamide or N-[(1R,2R)-1,2-diphenyl-2-(2-(4-methylbenzyloxy)ethylamino)ethyl]-4-methylbenzene sulfonamide.

Therefore, a further important configuration of the invention provides that the transition metal catalyst comprises at least one ligand selected from the group consisting of an optically active amine, in particular H$_2$N—CHPh-CHPh-OH, H$_2$N—CHMe-CHPh-OH, MeHN—CHMe-CHPh-OH, TsNH—CHPh-CHPh-NH$_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid; and is preferably selected from the group consisting of H$_2$N—CHPh-CHPh-OH, H$_2$N—CHMe-CHPh-OH, MeHN—CHMe-CHPh-OH, TsNH—CHPh-CHPh-NH$_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide. The preferred ligands are characterized in that they particularly readily form a complex with the transition metal. This transition metal complex is very stable under the conditions of the method according to the invention.

If the transition metal catalyst according to the invention comprises the ligands mentioned in the latter paragraph, a simple and efficient route is taken to prepare highly stereoisomerically enriched, or even stereoisomerically pure, cyclic α-ketoalcohols, particularly 6-hydroxycyclohexenones, in good yields from the corresponding cyclic α-ketoenols, particularly the corresponding 6-hydroxycyclohexadienones, as shown below.

For this reason, a particularly important development is also essential to the invention. This development comprises a method for preparing a cyclic α-ketoalcohol, in particular a 6-hydroxycyclohexenone, selected from the group consisting of 6-hydroxy-3-[(1E/Z)-3-hydroxy-3-methylpenta-1,4-dienyl]-2,4,4-trimethylcyclohex-2-en-1-one of the formula 1a and 6-hydroxy-3-[(1E/Z,3E/Z)-5-hydroxy-3-methylpenta-1,3-dienyl]-2,4,4-trimethylcyclohex-2-en-1-one of the formula 1b

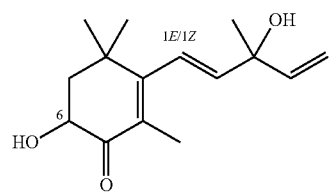

1a

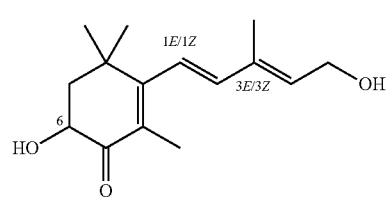

1b in which the asymmetric center in position 6 has (S) or (R) configuration, in which, in accordance with the invention, a cyclic α-ketoenol, in particular a 6-hydroxycyclohexadienone, selected from the group consisting of 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula 2b

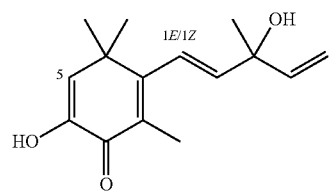

2a

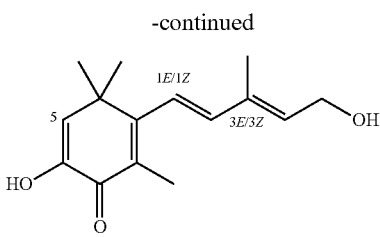

is reacted stereoselectively with a reducing agent selected from the group consisting of formic acid, the salts of formic acid, isopropanol or butan-2-ol, in the presence of an optically active, preferably an enantiomerically pure, transition metal catalyst, wherein the optically active, preferably the enantiomerically pure transition metal catalyst comprises ruthenium (Ru) as transition metal and at least one ligand selected from the group consisting of H$_2$N—CHPh-CHPh-OH, H$_2$N—CHMe-CHPh-OH, MeHN—CHMe-CHPh-OH, TsNH—CHPh-CHPh-NH$_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid.

The other stereoisomers in each case, i.e. the other enantiomer in each case or the diastereomers of the α-ketoalcohol, particularly the stereoisomers of the 6-hydroxycyclohexenone, only occur in very low amounts in this method and preferably not at all.

For example, if (1S,2S)—N-p-toluenesulfonyl-1,2-diphenylethylenediamine is used as optically active ligand in the method according to the invention, the compound of the formula (6S-1a/b) is obtained in high enantiomeric purity, while the use of (1R,2R)—N-p-toluenesulfonyl-1,2-diphenylethylenediamine as optically active ligand generates the compound of the formula (6R-1a/b).

In the method according to the invention, it has been found that most of the transition metal catalysts, including most of the chiral transition metal catalysts, are particularly efficient if at least one ligand thereof is mono-deprotonated.

Particular preference is also given to a chiral ruthenium catalyst, in which the optically active ligand is obtainable by mono-deprotonation of H$_2$N—CHPh-CHPh-OH, H$_2$N—CHMe-CHPh-OH, MeHN—CHMe-CHPh-OH or TsNH—CHPh-CHPh-NH$_2$, in particular by mono-deprotonation of (1S,2S)—N-p-toluenesulfonyl-1,2-diphenylethylenediamine or (1R,2R)—N-p-toluenesulfonyl-1,2-diphenylethylenediamine.

Thus, a configuration of the method according to the invention provides that the ligand, particularly the ligand selected from amines, is deprotonated, preferably mono-deprotonated.

In a modified embodiment, the method according to the invention provides that the transition metal catalyst comprises at least one ligand selected from the group consisting of H$_2$N—CH$_2$—CH$_2$—OH, MeHN—CH$_2$—CH$_2$—OH, H$_2$N—CH$_2$—CH$_2$—NH$_2$, TsNH—CH$_2$—CH$_2$—NH$_2$, TsNH—CH$_2$—CH$_2$—NH—(CH$_2$)$_n$—O$_m$—(CH$_2$)$_o$-aryl where n=1-4, m=0 or 1 and o=1-4 and aryl=phenyl or mono-, di-, tri-C1-C4-alkylphenyl, optically active chiral unit, wherein this ligand is linked to an aromatic compound optionally via a linker.

A further configuration of the method according to the invention specifies that the transition metal catalyst comprises at least one ligand selected from the group consisting of an optically active amine, in particular H$_2$N—CHPh-CHPh-OH, H$_2$N—CHMe-CHPh-OH, MeHN—CHMe-CHPh-OH, TsNH—CHPh-CHPh-NH$_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid; and is preferably selected from the group consisting of H$_2$N—CHPh-CHPh-OH, H$_2$N—CHMe-CHPh-OH, MeHN—CHMe-CHPh-OH, TsNH—CHPh-CHPh-NH$_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino) ethyl]-4-methylbenzene sulfonamide, N-[(1R,2R)-1,2-diphenyl-2-(2-(4-methylbenzyloxy)ethylamino)ethyl]-4-methylbenzene sulfonamide, wherein this ligand is linked to an aromatic compound optionally via a linker.

To remove transition metal catalysts from a reaction mixture, an additional filtration or extraction step is required. This step is essential for many of these transition metal catalysts since they would partially or totally lose their catalytic activity in any fixing or immobilizing process. Some transition metal catalysts are not, however, affected by such fixing.

Thus, a very economically designed variant of the method according to the invention provides that the transition metal is applied to a solid support; preferably to a solid support comprising at least one substance selected from the group consisting of carbon, aluminum oxide and silicon dioxide; and most preferably to a solid support constructed from at least one substance selected from the group consisting of carbon, aluminum oxide and silicon dioxide.

By means of this embodiment, a separation of the transition metal catalyst from the α-ketoalcohol reaction product, particularly from the 6-hydroxycyclohexenone and in particular the compounds 1a, 1b, is avoided in the sense of a separate method step.

The reduction of α-ketoenols, particularly of 6-hydroxycyclohexadienones such as the compounds 2a, 2b, was investigated at very different pH values with the result that a complete, or virtually complete, reaction to the corresponding α-ketoalcohol is possible only in a basic medium.

A further aspect of the invention, therefore, provides that α-ketoenols, in particular a 6-hydroxycyclohexadienone, is reacted non-stereoselectively or stereoselectively with a reducing agent under basic conditions, preferably in a pH range of 8 to 12.

Either the amine ligands already given above serve as bases and/or base is additionally added.

The base used, particularly as additional base, is ammonia, trimethylamine, triethylamine, tri-n-propylamine, tri-n-butylamine, diisopropylethylamine or a mixture of at least two of these compounds.

Therefore, a further refined embodiment of the invention specifies that α-ketoenols, in particular a 6-hydroxycyclohexadienone, is reacted non-stereoselectively or stereoselectively with a reducing agent under basic conditions, preferably in a pH range of 8 to 12, wherein the bases used for this purpose are selected from the group consisting of ammonia, trimethylamine, triethylamine, tri-n-propylamine, tri-n-butylamine, diisopropylethylamine or a mixture of at least two of these compounds.

In particular, this signifies provision of a method for preparing a cyclic α-ketoalcohol, in particular a 6-hydroxycyclohexenone, selected from the group consisting of 6-hydroxy-3-[(1E/Z)-3-hydroxy-3-methylpenta-1,4-dienyl]-2,4,4-trimethylcyclohex-2-en-1-one of the formula 1a and 6-hydroxy-3-[(1E/Z,3E/Z)-5-hydroxy-3-methylpenta-1,3-dienyl]-2,4,4-trimethylcyclohex-2-en-1-one of the formula 1b

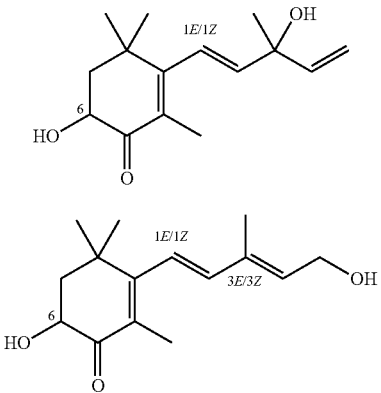

1a

1b in which the asymmetric center in position 6 is racemic or has (S) or (R) configuration, in which, in accordance with the invention, a cyclic α-ketoenol, in particular a 6-hydroxycyclohexadienone, selected from the group consisting of 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula 2b

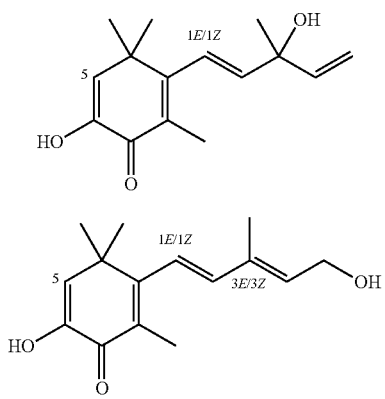

2a

2b is reacted non-stereoselectively or stereoselectively, under basic conditions, preferably in a pH range of 8 to 12, with a reducing agent selected from the group consisting of formic acid and/or the salts of formic acid, isopropanol, butan-2-ol, in the presence of a transition metal catalyst, wherein the transition metal catalyst comprises ruthenium (Ru) as transition metal and at least one ligand selected from the group consisting of $H_2N$—$CH_2$—$CH_2$—OH, MeHN—$CH_2$—$CH_2$—OH, $H_2N$—$CH_2$—$CH_2$—$NH_2$, TsNH—$CH_2$—$CH_2$—$NH_2$, TsNH—$CH_2$—$CH_2$—NH—$(CH_2)_n$—$O_m$—$(CH_2)_o$-aryl where n=1-4, m=0 or 1 and o=1-4 and aryl=phenyl or mono-, di-, tri-C1-C4-alkylphenyl, optically active compound.

A variant for bringing about enantiomerically or diastereomerically enriched, or enantiomerically or diastereomerically pure compounds, is provided by a method for preparing a cyclic α-ketoalcohol, in particular a 6-hydroxycyclohexenone, selected from the group consisting of 6-hydroxy-3-[(1E/Z)-3-hydroxy-3-methylpenta-1,4-dienyl]-2,4,4-trimethylcyclohex-2-en-1-one of the formula 1a and 6-hydroxy-3-[(1E/Z,3E/Z)-5-hydroxy-3-methylpenta-1,3-dienyl]-2,4,4-trimethylcyclohex-2-en-1-one of the formula 1b

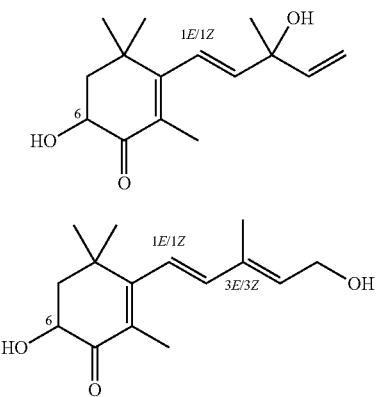

1a

1b in which the asymmetric center in position 6 has (S) or (R) configuration, in which, in accordance with the invention, a cyclic α-ketoenol, in particular a 6-hydroxycyclohexadienone, selected from the group consisting of 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula 2b

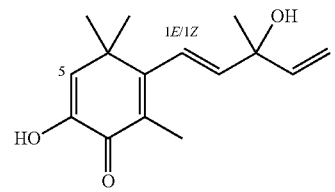

2a

2b is reacted stereoselectively under basic conditions, preferably in a pH range of 8 to 12, with a reducing agent selected from the group consisting of formic acid, the salts of formic acid, isopropanol or butan-2-ol, in the presence of an optically active transition metal catalyst, wherein the optically active transition metal catalyst comprises ruthenium (Ru) as transition metal and at least one ligand selected from the group consisting of $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)amino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid.

If an inventive transition metal catalyst is unable to maintain its activity in supported form, it has to be used in liquid phase.

Therefore, the method according to the invention is in many cases typically carried out in liquid phase, i.e. in at least one solvent or solvent mixture. The liquid phase preferably comprises at least one organic solvent, in which the liquid phase is typically composed of more than 50% by volume of organic solvent.

A further-developed variant of the invention therefore provides that the cyclic α-ketoenol, in particular the 6-hydroxycyclohexadienone, is reacted non-stereoselectively or stereoselectively with a reducing agent in a liquid medium, preferably in a liquid medium comprising more than 50% by volume of at least one organic solvent.

A liquid medium is understood to mean any monophasic or multiphasic liquid composition of a solvent or a solvent mixture. The liquid medium, therefore, is selected from the group of dichloromethane, ethylene glycol dimethyl ether, diethylene glycol dimethyl ether, tetrahydrofuran, acetonitrile, ethylene carbonate, propylene carbonate, dimethylformamide, dimethyl sulfoxide, ethyl acetate, n-propyl acetate, toluene, xylene, heptane, hexane, pentane, N-methyl-2-pyrrolidone, dioxane, 2-methyltetrahydrofuran, methyl tert-butyl ether, diisopropyl ether, diethyl ether, di-n-butyl ether, water or a mixture of at least two of these solvents.

If the proportion of organic solvent is selected to be greater than 50% by volume, the reaction reactants and reaction products dissolve relatively well.

In the reaction of the 6-hydroxycyclohexadienone with the reducing agent in the presence of the transition metal catalyst, salts often occur, specifically in a reaction under basic conditions. These usually dissolve well in water and can then be readily removed. The liquid medium can, therefore, particularly comprise water as inorganic solvent.

A further variant of the method according to the invention therefore specifies that the cyclic α-ketoenol, in particular the 6-hydroxycyclohexadienone, is reacted non-stereoselectively or stereoselectively with a reducing agent in a liquid medium, preferably in a liquid medium comprising more than 50% by volume of at least one organic solvent and comprising water as inorganic solvent.

Depending on the composition of the liquid medium composed of different solvents, the liquid medium may be a monophasic, biphasic or also multiphasic system.

Solubilities and therefore reaction rates differ from starting compound to starting compound. In various experiments, however, some solvents or mixtures thereof have been found to be particularly suitable. The solvents used are particularly mixtures of dichloromethane, ethylene glycol dimethyl ether, diethylene glycol dimethyl ether, and also THF and water.

Consequently, a development of the invention provides that the organic solvent comprises at least one compound selected from the group consisting of dichloromethane, ethylene glycol dimethyl ether, diethylene glycol dimethyl ether, tetrahydrofuran, ethylene carbonate, propylene carbonate, dimethylformamide, dimethyl sulfoxide, ethyl acetate, n-propyl acetate, toluene, xylene, heptane, hexane, pentane, N-methyl-2-pyrrolidone, dioxane, 2-methyltetrahydrofuran, methyl tert-butyl ether, diisopropyl ether, diethyl ether, di-n-butyl ether, acetonitrile and preferably from the group consisting of dichloromethane, ethylene glycol dimethyl ether, diethylene glycol dimethyl ether, tetrahydrofuran, acetonitrile, ethylene carbonate and propylene carbonate.

In various experiments, the following embodiment has proven to be particularly suitable with regard to yield and purity of the cyclic α-ketoalcohol obtained. Said embodiment specifies that the cyclic α-ketoenol, in particular the 6-hydroxycyclohexadienone, is reacted non-stereoselectively or stereoselectively with a reducing agent in a liquid medium, preferably in a liquid medium comprising more than 50% by volume of at least one organic solvent selected from the group consisting of dichloromethane, ethylene glycol dimethyl ether, diethylene glycol dimethyl ether, tetrahydrofuran, acetonitrile, propylene carbonate, ethylene carbonate and comprising water as inorganic solvent.

Another continuation of the invention results in high yields after a brief reaction time. Said continuation comprises a method for preparing a cyclic α-ketoalcohol, in particular a 6-hydroxycyclohexenone, selected from the group consisting of 6-hydroxy-3-[(1E/Z)-3-hydroxy-3-methylpenta-1,4-dienyl]-2,4,4-trimethylcyclohex-2-en-1-one of the formula 1a and 6-hydroxy-3-[(1E/Z,3E/Z)-5-hydroxy-3-methylpenta-1,3-dienyl]-2,4,4-trimethylcyclohex-2-en-1-one of the formula 1b

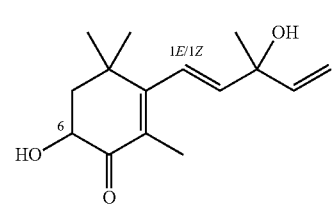

1a

1b in which the asymmetric center in position 6 is racemic or has (S) or (R) configuration, in which, in accordance with the invention, a cyclic α-ketoenol, in particular a 6-hydroxycyclohexadienone, selected from the group consisting of 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula 2b

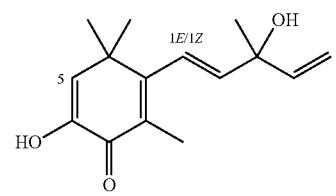

2a

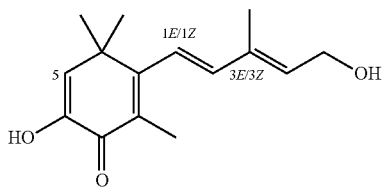

2b

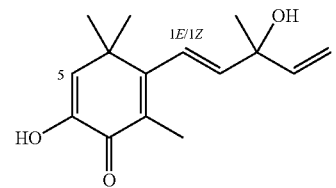

2a

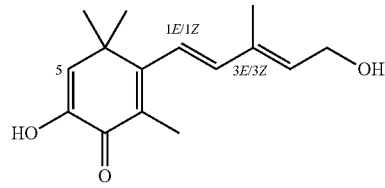

2b is reacted non-stereoselectively or stereoselectively in a liquid medium under basic conditions, preferably in a pH range of 8 to 12, with a reducing agent selected from the group consisting of formic acid and/or the salts of formic acid, isopropanol, butan-2-ol, in the presence of a transition metal catalyst, wherein the transition metal catalyst comprises ruthenium (Ru) as transition metal and at least one ligand selected from the group consisting of H₂N—CH₂—CH₂—OH, MeHN—CH₂—CH₂—OH, H₂N—CH₂—CH₂—NH₂, TsNH—CH₂—CH₂—NH₂, TsNH—CH₂—CH₂—NH—(CH₂)ₙ—Oₘ—(CH₂)ₒ-aryl where n=1-4, m=0 or 1 and o=1-4 and aryl=phenyl or mono-, di-, tri-C1-C4-alkylphenyl, optically active compound, and wherein the liquid medium comprises more than 50% by volume of at least one organic solvent selected from the group consisting of dichloromethane, ethylene glycol dimethyl ether, diethylene glycol dimethyl ether, tetrahydrofuran, acetonitrile, propylene carbonate, ethylene carbonate.

This applies also to the variant for generating highly enantiomerically or diastereomerically enriched compounds or enantiomerically or diastereomerically pure compounds. Said variant describes a method for preparing a cyclic α-ketoalcohol, in particular a 6-hydroxycyclohexenone, selected from the group consisting of 6-hydroxy-3-[(1E/Z)-3-hydroxy-3-methylpenta-1,4-dienyl]-2,4,4-trimethylcyclohex-2-en-1-one of the formula 1a and 6-hydroxy-3-[(1E/Z, 3E/Z)-5-hydroxy-3-methylpenta-1,3-dienyl]-2,4,4-trimethylcyclohex-2-en-1-one of the formula 1 b

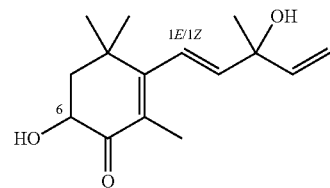

1a

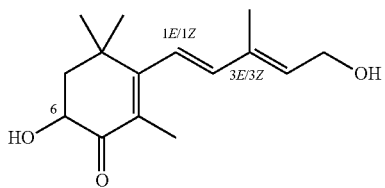

1b in which the asymmetric center in position 6 has (S) or (R) configuration, in which, in accordance with the invention, a cyclic α-ketoenol, in particular a 6-hydroxycyclohexadienone, selected from the group consisting of 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula 2b is reacted stereoselectively in a liquid medium under basic conditions, preferably in a pH range of 8 to 12, with a reducing agent selected from the group consisting of formic acid, the salts of formic acid, isopropanol or butan-2-ol, in the presence of an optically active transition metal catalyst, wherein the optically active transition metal catalyst comprises ruthenium (Ru) as transition metal and at least one ligand selected from the group consisting of H₂N—CHPh-CHPh-OH, H₂N—CHMe-CHPh-OH, MeHN—CHMe-CHPh-OH, TsNH—CHPh-CHPh-NH₂, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl-2-(2-(4-methylbenzyloxy)ethylamino)ethyl]-4-methylbenzene sulfonamide, an optically active amino acid and wherein the liquid medium comprises more than 50% by volume of at least one organic solvent selected from the group consisting of dichloromethane, ethylene glycol dimethyl ether, diethylene glycol dimethyl ether, tetrahydrofuran, acetonitrile, propylene carbonate, ethylene carbonate.

A further advantage of the method according to the invention is that said method affords high yields of cyclic α-ketoalcohol or 6-hydroxycyclohexenone even at low temperatures in a reasonable time. Consequently, the subject matter of a further modification of the invention is that the cyclic α-ketoenol, in particular the 6-hydroxycyclohexadienone, is reacted non-stereoselectively or stereoselectively with a reducing agent at a temperature of 10° C. to 85° C.; preferably 20° C. to 60° C.

The method according to the invention may also of course be carried out under pressure. The preferred pressure range is between 0 and 10 bar. The particularly preferred temperature range also under pressure is from 20 to 60° C.

The reaction may be carried out discontinuously in batch or semi-batch mode or continuously in the customary apparatus known to those skilled in the art. Examples include stirred tank, stirred tank cascade and tubular reactors.

The workup is also carried out by customary methods. Preference is given to extraction and crystallization.

The present invention also relates to a method for preparing (3S, 3'S)-astaxanthin in which, in a reaction step of the overall synthesis of (3S, 3'S)-astaxanthin, the above-described compound of the formula (6S-1a/b) is prepared by the method according to the invention. Analogously, (3R, 3'R)-astaxanthin may be prepared using a compound of the formula (6R-1a/b). The advantage of the method according to the invention lies in the simplified production of compounds of the formulae (6S-1a/b) and (6R-1a/b) with high enantiomeric purity coupled with good yields of these compounds. While the numbering in the compounds of the formulae 1a/b, 2a/b, i.e. 1a, 1b, 2a and 2b, is such that the cyclic OH group is located in position 6, the numbering in the compounds of astaxanthin 4a, 4b and 4c is such that the cyclic OH group is located in position 3 or 3' in the respective astaxanthin molecule.

The compounds generated by the method according to the invention can be used as precursor molecules for various carotenoids, inter alia, also for the synthesis of astaxanthin, in which the term astaxanthin refers to racemic mixtures and meso forms and all enantiomerically pure representatives of astaxanthin.

Consequently, the invention also relates to the use of the 6-hydroxycyclohexadienone selected from the group consisting of the compound 6-hydroxy-3-[(1E/Z)-3-hydroxy-3-methylpenta-1,4-dienyl]-2,4,4-trimethylcyclohexa-2,5-dien-1-one of the formula 2a and 6-hydroxy-3-[(1E/Z,3E/Z)-5-hydroxy-3-methylpenta-1,3-dienyl]-2,4,4-trimethylcyclohexa-2,5-dien-1-one of the formula 2b as an intermediate for preparing (3R/S, 3'R/S)-astaxanthin 4a,

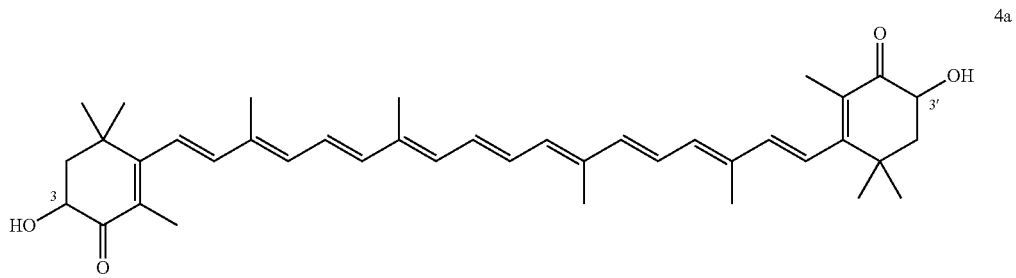

(3R/S, 3'R/S)-Astaxanthin and/or (3S, 3'S)-astaxanthin 4b,

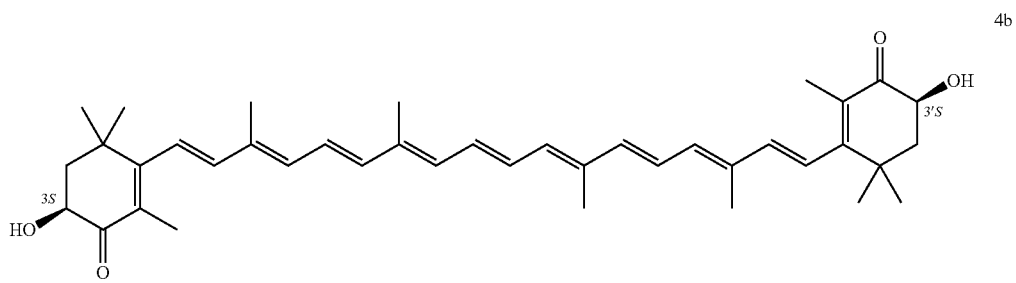

(3S, 3'S)-Astaxanthin and/or (3R, 3'R)-astaxanthin 4c

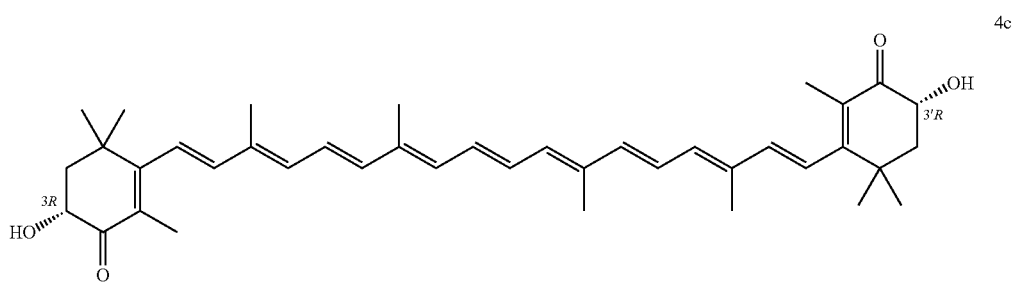

(3R, 3'R)-Astaxanthin

Further characteristics, details and advantages of the invention are apparent from the wording of the claims and also from the working examples described below.

EXAMPLES

Example 1: Synthesis of (6R/S)-hydroxy-3-[(1E/Z)-3-hydroxy-3-methylpenta-1,4-dienyl]-2,4,4-trimethylcyclohex-2-en-1-one (rac-1a)

2.5 g (9.77 mmol) of 6-hydroxy-3-[(1E/Z)-3-hydroxy-3-methylpenta-1,4-dienyl]-2,4,4-trimethylcyclohexa-2,5-dien-1-one 2a are charged in 13.36 g of degassed dichloromethane at 20° C. and 7.42 g (73.3 mmol) of triethylamine are added. 47.41 mg (0.1 mmol) of the catalyst chloro{[2-aminoethyl](4-toluenesulfonyl)amido}(p-cymene)ruthenium(II) are dissolved in 1 ml of dichloromethane and are added to the reaction mixture at 22° C. 2.25 g (48.87 mmol) of formic acid are then added dropwise at 20-27° C. over 12 min. The mixture is stirred overnight at 20° C. After addition of 10 ml of water, the phases are separated. The organic phase is washed twice with 10 ml of water and concentrated on a rotary evaporator. 2.45 g (84.87% strength, yield: 85%) of racemic 6-hydroxy-3-[(1E/Z)-3-hydroxy-3-methylpenta-1,4-dienyl]-2,4,4-trimethylcyclohex-2-en-1-one (rac-1a) are obtained.

Example 2: Synthesis of (6S)-hydroxy-3-[(1E/Z)-3-hydroxy-3-methylpenta-1,4-dienyl]-2,4,4-trimethylcyclohex-2-en-1-one (6S-1a) with DIGLYME and potassium formate 7.97 g of a 10% aqueous sodium hydroxide solution and 10 ml of water, and 8.38 g (99.57 mmol) of potassium formate are charged in a 100 ml 3-necked flask under argon and 30.5 g of saturated sodium hydrogen carbonate solution are added. To this solution are added 2.5 g (9.96 mmmol) of 6-hydroxy-3-[(1E/Z)-3-hydroxy-3-methylpenta-1,4-dienyl]-2,4,4-trimethylcyclohexa-2,5-dien-1-one 2a and 5 ml of diethylene glycol dimethyl ether (DIGLYME) and the mixture is heated to 40° C. To this are added 2.88 g of catalyst solution consisting of 36.49 mg (0.1 mmol) of (1S,2S)-(+)-N-p-tosyl-1,2-diphenylethylenediamine and 30.49 mg (0.05 mmol) of dichloro(p-cymene)ruthenium(II) dimer in diethylene glycol dimethyl ether (DIGLYME) and the mixture is stirred at 40° C. for 135 min. After cooling to 20° C., 20 ml of dichloromethane are added and the phases are separated. The aqueous phase is extracted twice with 10 ml of dichloromethane each time and the combined organic phases are then washed with 20 ml of water. The product is obtained by evaporation of the solvent. 8.6 g (yield 76.9%) of (6S)-hydroxy-3-[(1E/Z)-3-hydroxy-3-methylpenta-1,4-dienyl]-2,4,4-trimethylcyclohex-2-en-1-one (6S-1a) are obtained. The enantiomeric excess is determined by chiral HPLC. The excess is 95% in favor of the (S) enantiomer.

Example 3: Synthesis of (6S)-hydroxy-3-[(1E/Z)-3-hydroxy-3-methylpenta-1,4-dienyl]-2,4,4-trimethylcyclohex-2-en-1-one (6S-1a) with dichloromethane and triethylammonium formate 126.06 g (1.25 mol) of triethylamine and 100 ml of water are charged in a 250 ml 3-necked flask under argon and 45.87 g (1 mol) of formic acid are then added dropwise at 20-40° C. over 20 min. After the addition of 25 g (99.66 mmol) of 6-hydroxy-3-[(1E/Z)-3-hydroxy-3-methylpenta-1,4-dienyl]-2,4,4-trimethylcyclohexa-2,5-dien-1-one 2a and 50 ml of dichloromethane, the mixture is heated to 30° C. and 634.05 mg (1 mmol) of chloro{[(1S,2S)-(+)-2-amino-1,2-diphenylethyl](4-toluenesulfonyl)amido}(p-cymene)ruthenium(II) dissolved in 10 ml of dichloromethane are added dropwise. The mixture is stirred at 30° C. for 195 min and is then cooled to 20° C. The phases are separated and the aqueous phase is extracted with 50 ml of dichloromethane. The combined organic phases are then washed with 100 ml of water. The organic phase is treated with 100 ml of water and is adjusted with 10.3 g of formic acid to a pH of 6.6. After phase separation, the organic phase is concentrated by rotary evaporation. 24.4 g (83.6% strength, yield: 81.8%) of (6S)-hydroxy-3-[(1E/Z)-3-hydroxy-3-methylpenta-1,4-dienyl]-2,4,4-trimethylcyclohex-2-en-1-one (6S-1a) with an enantiomeric excess of 96.7% are obtained.

Example 4: Synthesis of (6S)-hydroxy-3-[(1E/Z)-3-hydroxy-3-methylpenta-1,4-dienyl]-2,4,4-trimethylcyclohex-2-en-1-one (6S-1a) with dichloromethane and triethylammonium formate and a quarter of the amount of catalyst 2.5 g (9.77 mmol) of 6-hydroxy-3-[(1E/Z)-3-hydroxy-3-methylpenta-1,4-dienyl]-2,4,4-trimethylcyclohexa-2,5-dien-1-one 2a are dissolved in 13.36 g of dichloromethane, admixed with 7.42 g (73.3 mmol) of triethylamine and 15.55 mg (0.02 mmol) of chloro{[(1S,2S)-(+)-2-amino-1,2-diphenylethyl](4-toluenesulfonyl)amido}(p-cymene)ruthenium (II) dissolved in 0.5 ml of dichloromethane are added dropwise. After heating the mixture to 40° C., 2.25 g (48.87 mmol) of formic acid are added dropwise over a period of 8 min. The mixture is stirred at 40° C. for 27 h. The mixture is then cooled to 20° C., 10 ml of water are added, the phases are separated and the organic phase is washed twice with 10 ml of water. The organic phase is concentrated. 2.7 g (73.7% strength, yield: 81.3%) of (6S)-hydroxy-3-[(1E/Z)-3-hydroxy-3-methylpenta-1,4-dienyl]-2,4,4-trimethylcyclohex-2-en-1-one (6S-1a) with an enantiomeric excess of 93.9% are obtained.

Example 5: Synthesis of (6S)-hydroxy-3-[(1E/Z)-3-hydroxy-3-methylpenta-1,4-dienyl]-2,4,4-trimethylcyclohex-2-en-1-one (6S-1a) with N-[(1S,2S)-1,2-diphenyl-2-(2-(4-methylbenzyloxy)ethylamino)ethyl]-4-methylbenzene sulfonamide(chloro)ruthenium(II) as catalyst 2.5 g (9.96 mmol) of 6-hydroxy-3-[(1E/Z)-3-hydroxy-3-methylpenta-1,4-dienyl]-2,4,4-trimethylcyclohexa-2,5-dien-1-one 2a are dissolved in 13.36 g of dichloromethane, admixed with 7.56 g (74.7 mmol) of triethylamine and 2.29 g (49.8 mmol) of formic acid are added dropwise. 64.74 mg (0.1 mmol) of N-[(1S,2S)-1,2-diphenyl-2-(2-(4-methylbenzyloxy)ethylamino)ethyl]-4-methylbenzene sulfonamide (chloro)ruthenium(II) of the formula 5 dissolved in 1 ml of dichloromethane are then added and the mixture is stirred at 25° C. for 17 h. 20 ml of water are then added, the phases are separated and the organic phase is washed twice with 10 ml of water each time and concentrated. 2.44 g (80.55% strength, yield: 78.9%) of (6S)-hydroxy-3-[(1E/Z)-3-hydroxy-3-methylpenta-1,4-dienyl]-2,4,4-trimethylcyclohex-2-en-1-one (6S-1a) with an enantiomeric excess of 98.9% are obtained.

Example 6: Synthesis of (6R)-hydroxy-3-[(1E/Z)-3-hydroxy-3-methylpenta-1,4-dienyl]-2,4,4-trimethylcyclohex-2-en-1-one (6R-1a) with dichloromethane and triethylammonium formate 24.29 g (0.24 mol) of triethylamine are emulsified with 20 ml of water and 8.92 g (0.19 mol) of formic acid are then added dropwise. Following the addition of 10 ml of dichloromethane and 5 g (19.37 mmol) of 6-hydroxy-3-[(1E/Z)-3-hydroxy-3-methylpenta-1,4-dienyl]-2,4,4-trimethylcyclohexa-2,5-dien-1l-one 2a, 123.26 mg (0.19 mmol) of chloro{[(1R,2R)-(+)-2-amino-1,2-diphenylethyl](4-toluenesulfonyl)amido}(p-cymene)ruthenium(II) dissolved in 1 ml of dichloromethane are added dropwise at 30° C. and the mixture is stirred for 205 min. The catalyst is deactivated by the addition of 60.13 mg of 2-mercaptonicotinic acid, and the phases are separated at 20° C. The aqueous phase is extracted twice with 30 ml of dichloromethane each time and the combined organic phases are washed with 50 ml of a 10% strength acetic acid solution and then with 50 ml of a saturated sodium hydrogen carbonate solution. The organic phase is concentrated by rotary evaporation at 40° C. 5.1 g (85.2% strength, yield: 89.6%) of (6R)-hydroxy-3-[(1E/Z)-3-hydroxy-3-methylpenta-1,4-dienyl]-2,4,4-trimethylcyclohex-2-en-1-one (6R-1a) with an enantiomeric excess of 96.5% are obtained.

It can be seen that the invention relates to a method for preparing a cyclic α-ketoalcohol, particularly a 6-hydroxycyclohexenone from a cyclic α-ketoenol, particularly a 6-hydroxycyclohexadienone, using a reducing agent. This reducing agent is selected from hydrogen gas; a secondary alcohol, formic acid and the salts of formic acid or a mixture of at least two representatives of these compound classes. The invention further comprises the use of an α-ketoenol, in particular a 6-hydroxycyclohexadienone, as intermediate for preparing astaxanthin.

The invention claimed is:

1. A method for preparing a 6-hydroxycyclohexenone selected from the group consisting of 6-hydroxy-3-[(1E/Z)-3-hydroxy-3-methylpenta-1,4-dienyl]-2,4,4-trimethylcyclohex-2-en-1-one of the formula (1a) and 6-hydroxy-3-[(1E/Z,3E/Z)-5-hydroxy-3-methylpenta-1,3-dienyl]-2,4,4-trimethylcyclohex-2-en-1-one of the formula (1b)

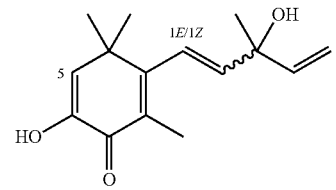

in which the asymmetric center in position 6 is racemic or has (S) or (R) configuration, wherein a 6-hydroxycyclohexadienone selected from the group consisting of 6-hydroxy-3-[(1E/Z)-3-hydroxy-3-methylpenta-1,4-dienyl]-2,4,4-trimethylcyclohexa-2,5-dien-1-one of the formula (2a) and 6-hydroxy-3-[(1E/Z,3E/Z)-5-hydroxy-3-methylpenta-1,3-dienyl]-2,4,4-trimethylcyclohexa-2,5-dien-1-one of the formula (2b)

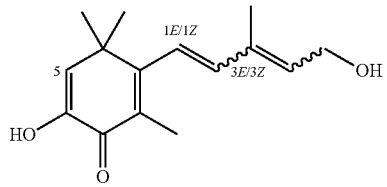

is reacted non-stereoselectively or stereoselectively with a reducing agent.

2. The method according to claim 1, wherein the reducing agent is at least one compound selected from the group consisting of hydrogen gas; a secondary alcohol; formic acid and the salts of formic acid.

3. The method according to claim 1, wherein the reducing agent is at least one compound selected from the group consisting of hydrogen gas; isopropanol or butan-2-ol; formic acid, an alkali metal, alkaline earth metal or ammonium formate or a mono-, di-, tri- or tetra(C1-C4)-alkylammonium formate.

4. The method according to claim 1, wherein the 6-hydroxycyclohexadienone is reacted non-stereoselectively or stereoselectively with the reducing agent in the presence of a transition metal catalyst.

5. The method according to claim 1, wherein the 6-hydroxycyclohexadienone is reacted non-stereoselectively or stereoselectively with the reducing agent in the presence of an achiral or optically active transition metal catalyst.

6. The method according to claim 3, wherein the transition metal catalyst comprises a transition metal selected from the group consisting of Ti, Zr, Hf, V, Nb, Ta, Cr, Mo, W, Mn, Re, Fe, Ru, Os, Co, Rh, Ir, Ni, Pd, Pt, Cu, Ag and Au.

7. The method according to claim 3, wherein the transition metal catalyst comprises a transition metal selected from the group consisting of Ru, Ir, Ni and Pd.

8. The method according to claim 3, wherein the transition metal catalyst comprises at least one ligand selected from amines and/or phosphanes.

9. The method according to claim 5, wherein the ligand is a phosphane of the general formula (3),

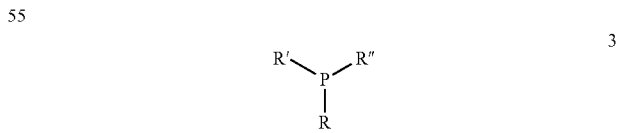

where R, R' and R" are each independently selected from the group consisting of at least one of the residues C1-C4-alkyl, phenyl, mono- up to tri-C1-C4-alkyl-substituted aryl and a triarylphosphane.

10. The method according to claim 5, wherein the ligand is a phosphane of the general formula (3),

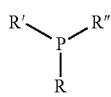

where R, R' and R" are each independently selected from the group consisting of a triphenylphosphane.

11. The method according to claim 3, wherein the transition metal catalyst comprises at least one ligand selected from the group consisting of $H_2N$—$CH_2$—$CH_2$—OH, MeHN—$CH_2$—$CH_2$—OH, $H_2N$—$CH_2$—$CH_2$—$NH_2$, TsNH—$CH_2$—$CH_2$—$NH_2$, TsNH—$CH_2$—$CH_2$—NH—$(CH_2)_n$—$O_m$—$(CH_2)_o$-aryl where n=1-4, m=0 or 1 and o=1-4 and aryl=phenyl or mono-, di-, tri-C1-C4-alkylphenyl, optically active compound.

12. The method according to claim 3, wherein the transition metal catalyst comprises at least one ligand selected from the group consisting of an optically active amine.

13. The method according to claim 3, wherein the transition metal catalyst comprises at least one ligand selected from the group consisting of $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluenesulfonyl-1,2-diphenylethylenediamine, (1R,2R)—N-p-toluenesulfonyl-1,2-diphenylethylenediamine, N-[(1S,2S)-1,2-diphenyl-2-(2-(4-methylbenzyloxy)ethylamino)ethyl]-4-methylbenzene sulfonamide, N-[(1R,2R)-1,2-diphenyl.

14. The method according to claim 5, wherein the ligand is deprotonated.

15. The method according to claim 4, wherein the transition metal is applied to a solid support comprising at least one substance selected from the group consisting of carbon, aluminum oxide and silicon dioxide.

16. The method according to claim 1, wherein the 6-hydroxycyclohexadienone is reacted non-stereoselectively or stereoselectively with a reducing agent under basic conditions.

17. The method according to claim 1, wherein the 6-hydroxycyclohexadienone is reacted non-stereoselectively or stereoselectively with a reducing agent in a liquid medium.

18. The method according to claim 17, wherein said liquid medium comprising more than 50% by volume of at least one organic solvent and said organic solvent comprises at least one compound selected from the group consisting of dichloromethane, ethylene glycol dimethyl ether, diethylene glycol dimethyl ether, tetrahydrofuran, ethylene carbonate, propylene carbonate, dimethylformamide, dimethyl sulfoxide, ethyl acetate, n-propyl acetate, toluene, xylene, heptane, hexane, pentane, N-methyl-2-pyrrolidone, dioxane, 2-methyltetrahydrofuran, methyl tert-butyl ether, diisopropyl ether, diethyl ether, di-n-butyl ether, acetonitrile and preferably from the group consisting of dichloromethane, ethylene glycol dimethyl ether, diethylene glycol dimethyl ether, tetrahydrofuran, acetonitrile, ethylene carbonate and propylene carbonate.

19. The method according to claim 1, wherein the 6-hydroxycyclohexadienone is reacted non-stereoselectively or stereoselectively with a reducing agent at a temperature of 10° C. to 85° C.

20. An intermediate for preparing (3R/S, 3'R/S))-astaxanthin (4a), (3S, 3'S)-astaxanthin (4b), and/or (3R, 3'R)-astaxanthin (4c)

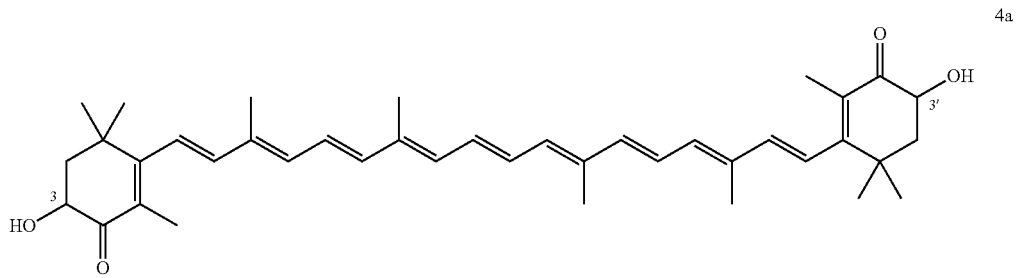

(3R/S, 3'R/S)-Astaxanthin

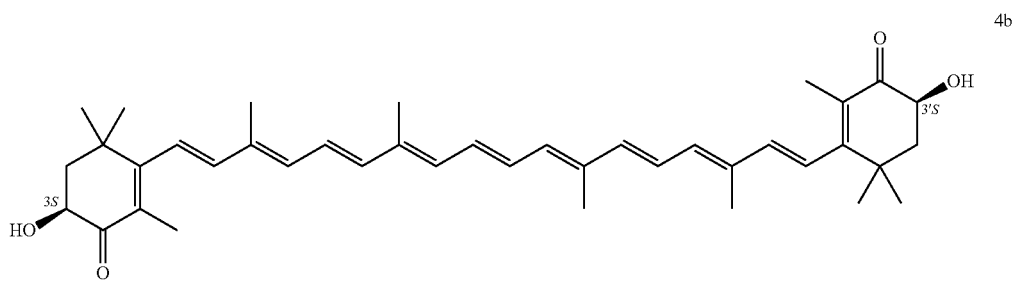

(3S, 3'S)-Astaxanthin

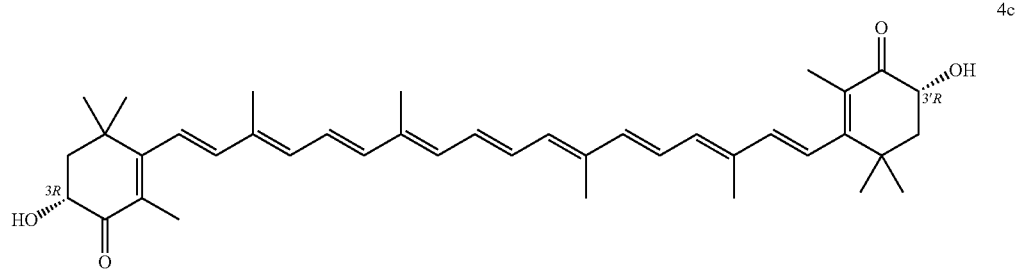
(3R, 3′R)-Astaxanthin
which comprises 6-hydroxy-3-[(1E/Z)-3-hydroxy-3-methyl-penta-1,4-dienyl]-2,4,4-trimethylcyclohexa-2,5-dien-1-one of the formula (2a).
21. A process for preparing (3R/S, 3′R/S))-astaxanthin (4a), (3S,3′S)-astaxanthin (4b), and/or (3R, 3′R)-astaxanthin (4c)
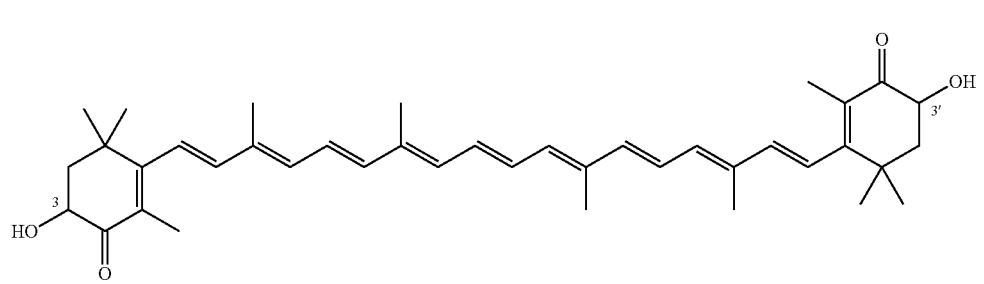
(3R/S, 3′R/S)-Astaxanthin
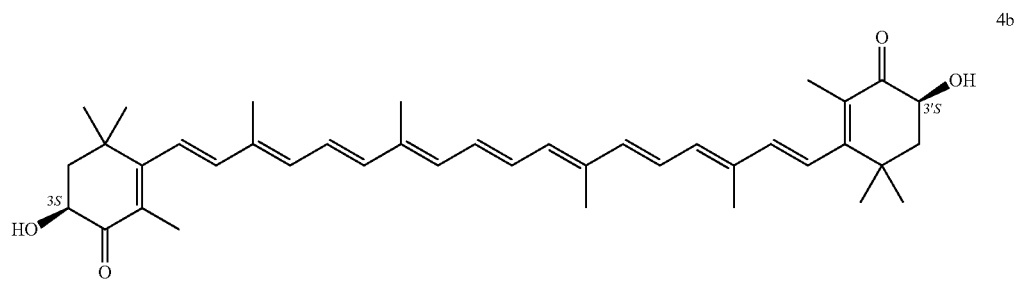
(3S, 3′S)-Astaxanthin
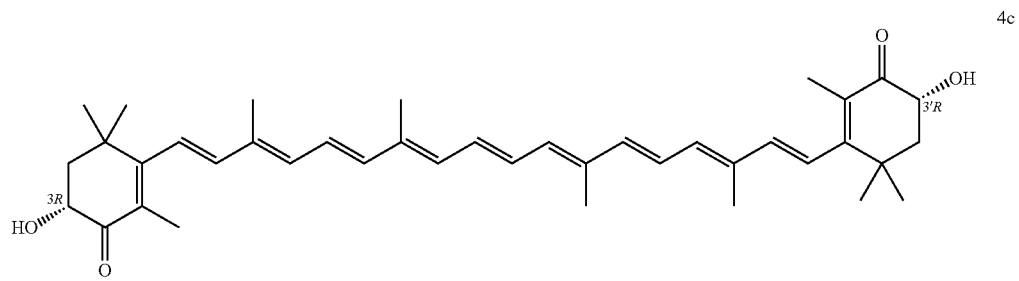
(3R, 3′R)-Astaxanthin which comprises utilizing the intermediate comprising 6-hydroxy-3-[(1E/Z)-3-hydroxy-3-methylpenta-1,4-dienyl]-2,4,4-trimethylcyclohexa-2,5-dien-1-one of the formula (2a) or 6-hydroxy-3-[(1E/Z,3E/Z)-5-hydroxy-3-methylpenta-1,3-dienyl]-2,4,4-trimethylcyclohexa-2,5-dien-1-one of the formula (2b).

22. The process as claimed in claim 21, wherein the compound of formula (2b) is used.

* * * * *